United States Patent [19]
Nolting

[11] Patent Number: 6,099,559
[45] Date of Patent: Aug. 8, 2000

[54] ENDOLUMINAL SUPPORT ASSEMBLY WITH CAPPED ENDS

[75] Inventor: John E. Nolting, Santa Rosa, Calif.

[73] Assignee: Medtronic Ave, Inc., Santa Rosa, Calif.

[21] Appl. No.: 09/086,781

[22] Filed: May 28, 1998

[51] Int. Cl.$^7$ ................................................. A61F 2/06
[52] U.S. Cl. ................................................. 623/1.16
[58] Field of Search ............................... 623/1, 11, 12; 606/194, 198, 153

[56] References Cited

U.S. PATENT DOCUMENTS

| | | | |
|---|---|---|---|
| 4,731,073 | 3/1988 | Robinson | 623/1 |
| 4,776,337 | 10/1988 | Palmaz | 128/343 |
| 4,994,071 | 2/1991 | MacGregor | 606/194 |
| 5,064,435 | 11/1991 | Porter . | |
| 5,123,917 | 6/1992 | Lee | 623/1 |
| 5,207,960 | 5/1993 | Moret de Rocheprise | 264/103 |
| 5,282,823 | 2/1994 | Schwartz | 606/198 |
| 5,282,860 | 2/1994 | Matsuno et al. | 623/12 |
| 5,330,500 | 7/1994 | Song | 606/198 |
| 5,360,443 | 11/1994 | Barone et al. | 623/1 |
| 5,383,892 | 1/1995 | Cardon et al. . | |

(List continued on next page.)

FOREIGN PATENT DOCUMENTS

| | | |
|---|---|---|
| 0 466 518 A2 | 1/1992 | European Pat. Off. . |
| 0 556 850 A1 | 8/1993 | European Pat. Off. . |
| 0 621 016 A1 | 10/1994 | European Pat. Off. . |
| 0 657 147 A3 | 6/1995 | European Pat. Off. . |
| 0 686 379 A2 | 12/1995 | European Pat. Off. . |
| 0 689 805 A3 | 3/1996 | European Pat. Off. . |
| 0 701 800 A1 | 3/1996 | European Pat. Off. . |
| 0 712 614 A1 | 5/1996 | European Pat. Off. . |
| 0 747 020 A3 | 11/1996 | European Pat. Off. . |
| 0 797 963 A2 | 1/1997 | European Pat. Off. . |
| 0 775 472 A2 | 5/1997 | European Pat. Off. . |
| 0 800 801 A1 | 10/1997 | European Pat. Off. . |
| 0 819 412 A2 | 1/1998 | European Pat. Off. . |
| WO 84/03036 | 8/1984 | WIPO . |
| WO 95/05132 | 2/1995 | WIPO . |
| WO 96/14808 | 5/1996 | WIPO . |
| WO 96/21404 | 7/1996 | WIPO . |
| WO 96/39104 | 12/1996 | WIPO . |

OTHER PUBLICATIONS

Jomed Internet Advertisement, "Jostent Coronary Stent Graft—The Best of Two Worlds", http://www.jomed.com/docs/graft1.htm, Oct. 16, 1997.

*Primary Examiner*—Mickey Yu
*Assistant Examiner*—Choon P. Koh
*Attorney, Agent, or Firm*—Richard L. Klein; Catherine C. Maresh; Deanna J. Shirley

[57] ABSTRACT

An endovascular support assembly, or stent assembly, and a covered endovascular support assembly, or stent-graft assembly, with caps on either or both ends for improved and uniform deployment of the assembly. Additionally, the caps serve to capture the graft material between the caps and the endovascular support device or stent.

20 Claims, 3 Drawing Sheets

U.S. PATENT DOCUMENTS

| | | | |
|---|---|---|---|
| 5,389,106 | 2/1995 | Tower | 606/198 |
| 5,443,496 | 8/1995 | Schwartz et al. | 623/1 |
| 5,449,382 | 9/1995 | Dayton | 623/1 |
| 5,489,295 | 2/1996 | Piplani | 623/1 |
| 5,507,771 | 4/1996 | Gianturco | 606/198 |
| 5,522,880 | 6/1996 | Barone et al. | 623/1 |
| 5,522,881 | 6/1996 | Lentz | 623/1 |
| 5,522,882 | 6/1996 | Gaterud et al. | 623/1 |
| 5,534,287 | 7/1996 | Lukic | 427/2.25 |
| 5,556,414 | 9/1996 | Turi | 606/198 |
| 5,562,728 | 10/1996 | Lazarus et al. | 623/1 |
| 5,571,173 | 11/1996 | Parodi | 623/1 |
| 5,578,071 | 11/1996 | Parodi | 623/1 |
| 5,578,072 | 11/1996 | Barone et al. | 623/1 |
| 5,609,627 | 3/1997 | Goicoechea et al. | |
| 5,628,785 | 5/1997 | Schwartz et al. | 623/1 |
| 5,628,786 | 5/1997 | Banas et al. | 623/1 |
| 5,628,788 | 5/1997 | Pinchuk | 623/1 |
| 5,632,772 | 5/1997 | Alcime et al. | 623/1 |
| 5,637,113 | 6/1997 | Tartaglia et al. | 623/1 |
| 5,639,278 | 6/1997 | Dereume et al. | 623/1 |
| 5,641,373 | 6/1997 | Shannon et al. | 156/242 |
| 5,645,559 | 7/1997 | Hachtman et al. | 606/198 |
| 5,653,743 | 8/1997 | Martin | 623/1 |
| 5,653,747 | 8/1997 | Dereume | 623/1 |
| 5,667,523 | 9/1997 | Bynon | 606/198 |
| 5,674,241 | 10/1997 | Bley et al. | 606/198 |
| 5,683,448 | 11/1997 | Cragg | 623/1 |
| 5,683,453 | 11/1997 | Palmaz | 623/1 |
| 5,700,285 | 12/1997 | Myers et al. | 623/1 |
| 5,713,917 | 2/1998 | Leonhardt et al. | 606/194 |
| 5,723,004 | 3/1998 | Dereume et al. | 623/1 |
| 5,735,892 | 4/1998 | Myers et al. | 623/1 |
| 5,749,880 | 5/1998 | Banas et al. | 606/198 |
| 5,916,264 | 6/1999 | Van Oepen et al. | 623/1 |

ENDOLUMINAL SUPPORT ASSEMBLY WITH CAPPED ENDS

FIELD OF THE INVENTION

This present invention relates generally to implantable devices for maintaining the patency of stenotic or diseased lumens. And, more specifically, to an endoluminal or covered endoluminal support assembly having additional support devices at either or both ends for more uniform deployment of the assembly.

BACKGROUND OF THE INVENTION

Cardiovascular disease is the leading cause of death in the United States. A number of methods have been developed for treating coronary heart disease. One common procedure is percutaneous transluminal coronary angioplasty ("PTCA"). PTCA typically involves advancing a catheter, having an inflatable balloon on the distal end thereof, through a patient's arterial system until the balloon crosses an atherosclerotic lesion. The balloon is then inflated to dilate the artery. After dilation, the balloon is deflated and the catheter removed leaving an enlarged arterial passageway or lumen, thereby increasing blood flow. A significant number of PTCA procedures, however, result in a restenosis or renarrowing of the lumen.

To lessen the risk of stenosis or restenosis of lumens, various endovascular devices have been proposed for mechanically keeping an affected lumen open after completion of procedures, such as PTCA. For purposes of the instant invention, the lumen to be treated is not limited to coronary arteries, but also includes any other similar body conduit that tends to improperly constrict as a result of disease or malfunction, such as: arteries located within the mesentery, peripheral, or cerebral vasculature; veins; gastrointestinal tract; biliary tract; urethra; trachea; hepatic shunts; and fallopian tubes.

Endovascular devices generally referred to as "stents," and covered endovascular support devices generally referred to as "stent-grafts," are typically inserted into the lumen, positioned across a lesion, and then expanded to keep the passageway clear. Effectively, the stent or stent-graft overcomes the natural tendency of some lumen walls to close due to restenosis, thereby maintaining a more normal flow of blood through that lumen than would be possible if the stent or stent-graft were not in place or if only a PTCA procedure were performed.

There are two general categories of stents, self-expanding stents and balloon-expandable stents. Some self-expanding stents are made from stainless steel wire or wire braid. Such stents are typically compressed into a first shape and inserted into a sheath or cartridge. During insertion, the stent is positioned along a delivery device, such as a catheter, that is extended to make the stent diameter as small as possible. When the stent is positioned across the lesion, the sheath is withdrawn causing the stent to radially expand and abut the vessel wall. Depending on the materials used in construction of the stent, the wire or wire braid maintains the new shape either through mechanical force or otherwise.

Another type of self-expanding stent is made from a shape-memory alloy such as NITINOL. This stent has been pre-treated to assume an expanded state at body temperature. Prior to delivery to the affected area, the stent is typically crimped or compressed near or below room temperature.

Balloon-expandable stents are typically introduced into a lumen on a catheter having an inflatable balloon on the distal end thereof. When the stent is at the desired location in the lumen, the balloon is inflated to circumferentially expand the stent. The balloon is then deflated and the catheter is withdrawn, leaving the circumferentially expanded stent in the lumen, usually as a permanent prosthesis for helping to hold the lumen open.

One type of balloon-expandable stent is a tubular-slotted stent, which involves what may be thought of as a tube having a number of slots cut in its wall, resulting in a mesh when expanded. A tubular-slotted stent is typically cut out of a hypo-tube, or out of a sheet, which is then rolled, and welded to form a the tube. Example of such stents include, but are not limited to, those disclosed in U.S. Pat. Nos. 4,733,665, 4,776,337, 4,739,762 and 5,102,417 all issued to Palmaz, U.S. Pat. No. 5,195,984 issued to Schatz, U.S. Pat. No. 5,421,955 issued to Lau et al., or U.S. Pat. No. 5,449,373 issued to Pinchasik et al.

A balloon-expandable stent referred to as a wire stent overcomes some of the problems associated with tubular-slotted stents. A wire stent is generally formed by winding a circular shaped wire into supportive elements, which typically have a circular cross-section. The problem with wire stents is that the supportive elements comprising the stent can axially displace with respect to each other, resulting in a stent that fails to provide adequate support.

U.S. Pat. Nos. 5,292,331 and 5,674,278 both issued to Boneau, which are hereby incorporated by reference, disclose another type of wire-like stent. This stent is made by taking a ring or toroid having a circular cross-section, and then forming the ring into a series of sinusoidally-shaped elements. While preferably employing a single piece of material, suitably welded wire is also acceptable. Such a stent has excellent radial strength while retaining the flexibility of wire stents. This endovascular support device may include a plurality of stents mounted on the balloon.

All these stent can be used alone or in conjunction with a covering or graft.

During a PTCA procedure as discussed above, atheromatous plaques undergo fissuring, thereby creating a thrombogenic environment in the lumen. Excessive scarring may also occur following the procedure, potentially resulting in reocclusion of the treated lumen. Attempts to address these problems include providing a suitable surface within the lumen for more controlled healing to occur in addition to the support provided by a stent. These attempts include providing a lining or covering in conjunction with a stent. The covering of a stent-graft may prevent excessive tissue prolapse or protrusion of tissue growth through the interstices of the stent while allowing limited tissue in-growth to occur to enhance the implantation. The surface of the graft material at the same time minimizes thrombosis, prevents scarring from occluding the lumen and minimizes the contact between the fissured plaque and the hematological elements in the bloodstream.

The stents, and stent-graft, assemblies are mounted on a balloon of a balloon catheter and forcibly expanded from pressure exerted during expansion of the balloon, as discussed above. These stents and stent-grafts are circumscribe most but not all of the length of the balloon. The exposed ends of the balloon, coupled with the fact that the ends of the stent or stent-graft will inherently deploy under less force than the medial portion thereof, results in the stent or stent-graft being deployed in a non-uniform fashion. More specifically, the ends of the stents begin to deploy prior to the reminder of the stent.

Further, with regard to prior art stent-grafts, much focus has been directed towards adhering or attaching the graft material to the stent.

SUMMARY OF THE INVENTION

The present invention provides a stent or stent-graft for helping to hold open a lumen. The stent or stent-graft comprises a first stent and at least one additional stent serving as an end cap at one or both ends of the first stent.

According to the assemblies described herein, the present invention increases the amount of pressure needed to circumferentially expand the ends of the assembly, thereby providing a more uniform deployment of the assembly.

Also according to the invention, the graft material or lining is sandwiched between the first stent and the end caps.

Therefore, it is an object of the instant invention to provide a stent or stent-graft assembly with more uniform deployment characteristics.

It is a further object of the invention to provide a stent-graft assembly with simply and positively attaches the graft material to the stent assembly.

DETAILED DESCRIPTION OF THE EMBODIMENTS

The present invention relates to a stent or stent-graft assembly having end caps which: cause a more uniform deployment of the assembly; and, in the case of a stent-graft, capture or sandwich the lining between the stent and the end caps. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments. Thus, the present invention is not intended to be limited to the embodiment shown but is to be accorded the widest scope consistent with the principles and features described herein.

Figure 1:
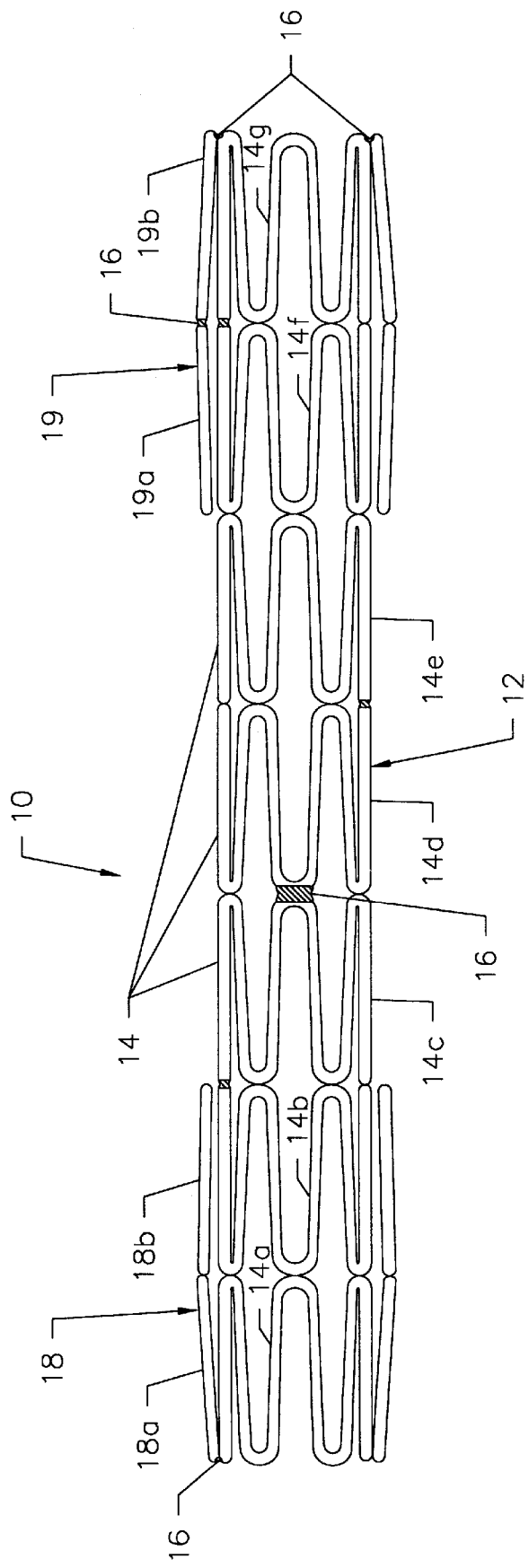
FIG. 1 is a side view of an illustrative embodiment of a stent assembly embodying the principles of the present invention.

FIG. 1 is a side view of an illustrative embodiment of the stent assembly according to the present invention. Stent assembly 10 includes a first stent 12 having a plurality of stent sections 14a–g, each of which is made of an endless metal loop that has been bent into a plurality of straight sections or struts that are integrally joined by discrete axial turns, or crowns. Each section 14 may have more or less undulations or crowns than are shown in FIG. 1, but the simplified depictions shown herein will be sufficient to illustrate the present invention.

Although sections 14a–g may or may not be made of what would be regarded in some other arts as wire, the material of sections 14a–g is generally wire-like, and so the term "wire" is sometimes used herein to refer to such stent material. Axially adjacent sections 14a–g may be joined to one another at one or more aligned crowns. These connections 16 (if and to the extent present) may be made by fusing, welding, soldering, adhesive bonding, mechanical fastening, or in any other suitable manner.

End caps 18 and 19 are disposed at both ends of stent 12. These end caps are essentially, and act as, second and third stents, and provide additional resistance to pressure at either end of stent assembly 10. This results in a more uniform expansion of the stent assembly under the influence of the expansion pressures exerted thereon from the balloon of the balloon catheter (not shown). Preferably, the length of each end cap is less than half of the length of first stent 12.

In the embodiment shown, end caps 18 and 19 each comprise two sections 18a, 18b and 19a and 19b, respectively, similar to stent sections 14. And are joined to each other in a similar manner. The end caps are joined to first stent 12 at both ends of stent 12 at one or more radially adjacent crowns.

A typical technique for delivering stents of the general type shown as reference numeral 12 in FIG. 1 into a lumen is to initially dispose of the stent assembly in a circumferentially compressed form around a deflated balloon a balloon catheter. The catheter is then inserted into a tubular body structure to be stented until the balloon and stent are at the desired location along the body structure. The balloon is then inflated to circumferentially expand the stent. Lastly, the balloon is deflated and the catheter is withdrawn, leaving the expanded stent behind in the body structure.

Typically, the balloon used is longer than the stent assembly, resulting in portions of the balloon extending proximally and distally of the stent assembly. Those exposed portions of the balloon tend to inflate prior to the remainder of the balloon which is circumferentially captured by the stent assembly. This causes uneven inflation of the balloon and deployment of the stent, with the ends of the stent assembly tending to deploy before the remaining or intermediate portion of the stent assembly. The end caps 18, 19 compensate for this by increasing the amount of pressure needed to deploy the ends of the stent assembly. Thereby, a more uniform deployment of the stent assembly is achieved.

Figure 2A:
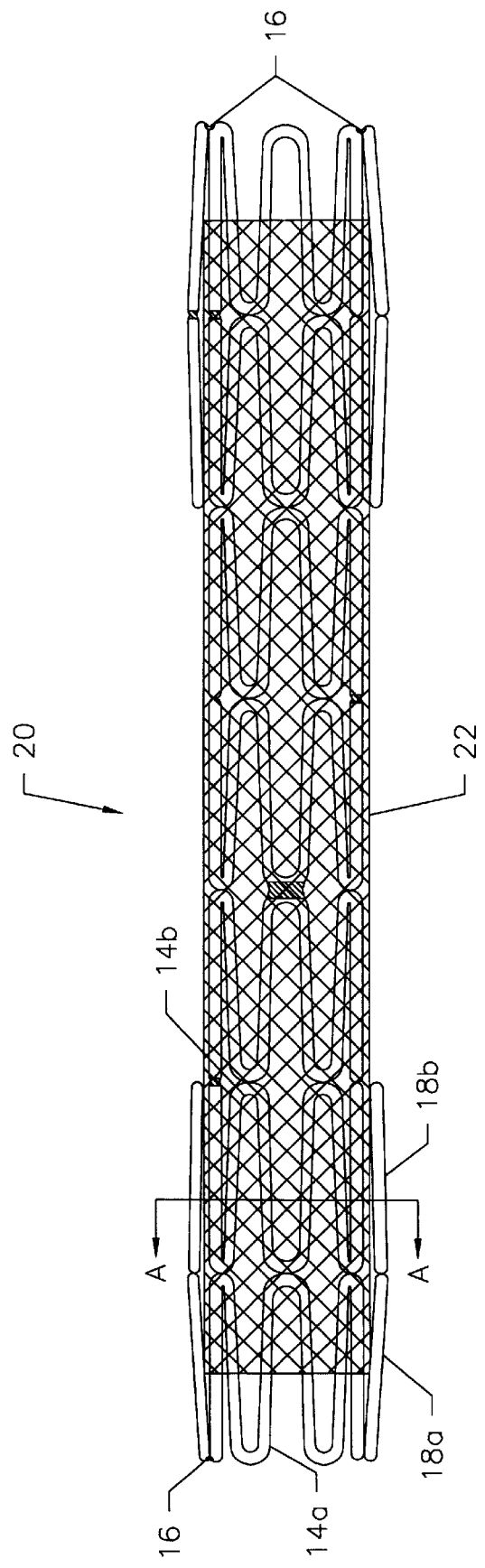
FIG. 2A is a side view of an illustrative embodiment of a stent-graft assembly embodying the principles of the present invention.
Figure 2B:
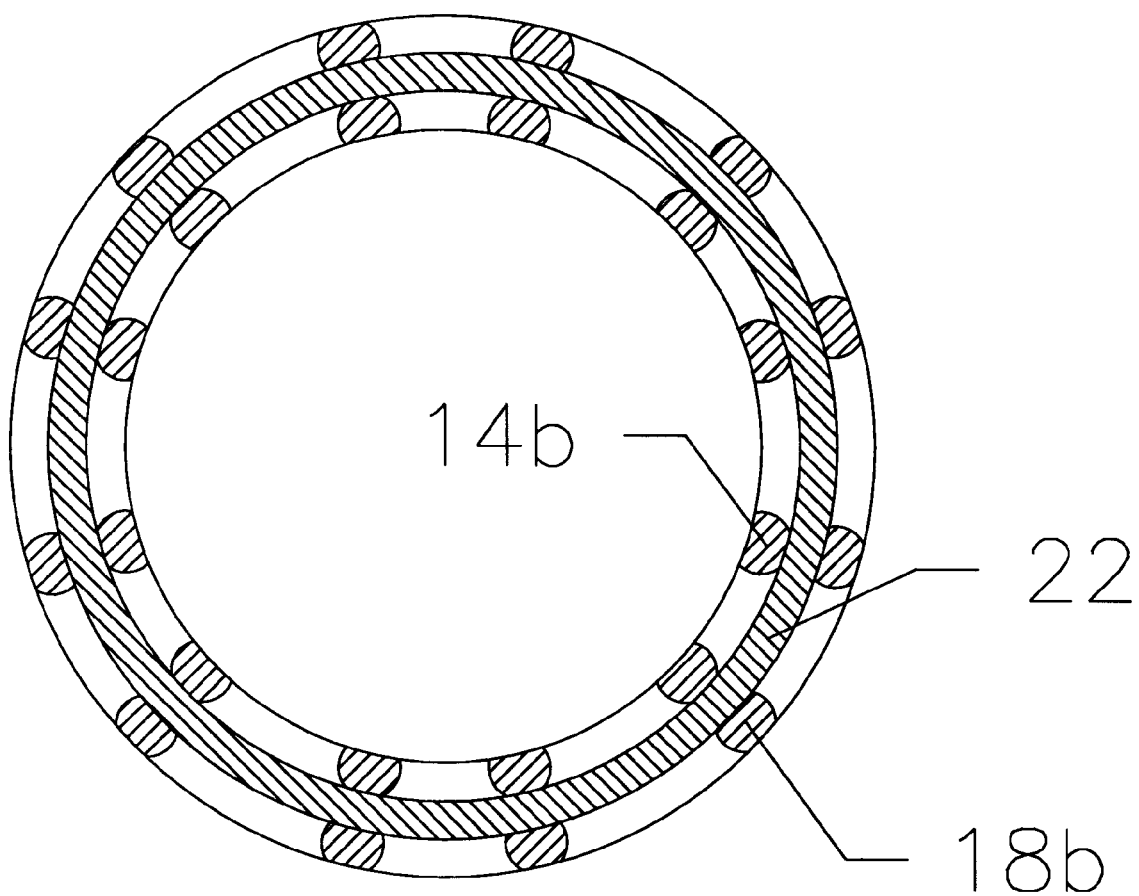
FIG. 2B is a cross-section view along line A—A of FIG. 2A.

Turning to FIGS. 2A and 2B, a stent-graft assembly 20 in accordance with the teachings of the invention is depicted. In this embodiment, a lining or graft material 22 is captured or sandwiched between the first stent 12 and end caps 18, 19. Stent 12, comprising stent sections 14a–f, and end caps 18a, 18b and 19a, 19b are similar to that discussed with respect to FIG. 1 above.

End cap sections 18a and 19b are connected to stent sections 14a and 14g, respectively. More specifically, the cap section is connected to the respective stent section at one or more radially adjacent crowns such as by fusing, welding, soldering, or in any other suitable manner.

Suitable material for the lining includes, but is not limited to, polyesters, polytetrafluoroethylene, polyurethane and silicone. Lining 22 is preferably sized so as to terminate halfway between the ends or crowns of stent sections 14a and 14g. This provides uniform support of the graft material at either end thereof. More specifically, if the lining were to terminate at or near the crowns, there would be greater unsupported distances of the lining at the leading edge of the graft.

A stent assembly with end caps for more uniform deployment of the assembly has been disclosed. A stent-graft assembly with end caps which also serves to capture the graft material has also been disclosed. Although the present invention has been described in accordance with the embodiments shown, one of ordinary skill in the art will readily recognize that there could be variations to the embodiments and those variations would be within the spirit and scope of the present invention.

For example, other means for increasing the resistance to pressure at either end of the stent assembly such as an elastomeric or polymeric sleeve may be employed. Additionally, stents of varying types can be used for the stent and the end caps or any combination thereof.

What is claimed is:

1. An endoluminal support assembly comprising:

a first generally cylindrical stent having a length, first and second ends, an exterior and an interior, and a medial region, said first generally cylindrical stent defining a passageway therethrough;

a second generally cylindrical stent having a length shorter than the length of the first stent and disposed radially outwardly and the second stent entirely overlapping a first end of the first stent.

2. The endoluminal support assembly according to claim 1 and further comprising a third generally cylindrical stent having a length less than the first stent length and disposed radially outwardly and the third stent entirely overlapping the second end of the first stent.

3. The endoluminal support assembly according to claim 2 wherein the second generally cylindrical stent is connected to the first stent at the first end of the first stent, and the third generally cylindrical stent is connected to the first stent at the second end of the first stent.

4. The endoluminal support assembly according to claim 2 wherein the length of second generally cylindrical stent and the length of the third generally cylindrical stent are each less than half of the length of the first stent.

5. An endoluminal support assembly for implantation into a lumen, comprising:

a generally cylindrical endovascular support device having a length, first and second ends, an exterior and an interior, and a medial region, said generally cylindrical endovascular support device defining a passageway therethrough and having a compressed configuration for delivery to a site in the lumen and an expanded configuration;

means for applying a force to the endovascular support device to form said expanded configuration; and means disposed entirely circumferentially about and along the exterior of one end of the endovascular support device for increasing the amount of force needed to expand said one end of the endovascular support device from the force needed to expand the medial region.

6. A stent-graft assembly comprising:

a first generally cylindrical stent having a length, first and second ends, an exterior and an interior, and a medial region, said first generally cylindrical stent defining a passageway therethrough;

a second generally cylindrical stent disposed radially outwardly and overlapping the first end of the first stent; and a lining having a first and second end and covering at least a portion of the exterior of the first stent, and having one end thereof disposed between the first and second stents.

7. The stent-graft assembly according to claim 6 and further comprising a third generally cylindrical stent having a length and disposed radially outwardly and overlapping the second end of the first stent.

8. The stent-graft assembly according to claim 7 wherein the first end of lining is disposed between the first and second stents and the second end of the lining is disposed between the first and third stents.

9. The stent-graft assembly according to claim 7 wherein the second generally cylindrical stent is connected to the first stent at the first end of the first stent, and the third generally cylindrical stent is connected to the first stent at the second end of the first stent.

10. The stent-graft assembly according to claim 7 wherein the length of second generally cylindrical stent and the length of the third generally cylindrical stent are each less than half of the length of the first stent.

11. The stent-graft assembly according to claim 6 wherein the lining is a polymer selected from the group consisting of polyurethane, ePTFE, dimethyl terephthalate, polyester, polyethylene terephthalate and silicone.

12. An endoluminal support assembly comprising:

a first generally cylindrical stent having a length, first and second ends, an exterior and an interior, and a medial region, said first generally cylindrical stent defining a passageway therethrough;

a second generally cylindrical stent having a length and disposed radially outwardly and the second stent entirely overlapping one end of the first stent; and a third generally cylindrical stent having a length and disposed radially outwardly and the third stent entirely overlapping the second end of the first stent.

13. The endoluminal support assembly according to claim 12 wherein the second generally cylindrical stent is connected to the first stent at the first end of the first stent, and the third generally cylindrical stent is connected to the first stent at the second end of the first stent.

14. The endoluminal support assembly according to claim 12 wherein the length of second generally cylindrical stent and the length of the third generally cylindrical stent are each less than half of the length of the first stent.

15. An endoluminal support assembly for implantation into a lumen, comprising:

a generally cylindrical endovascular support device having a length, first and second ends, an exterior and an interior, and a medial region, said generally cylindrical endovascular support device defining a passageway therethrough and having a compressed configuration for delivery to a site in the lumen and an expanded configuration;

means for applying a force to the endovascular support device to form said expanded configuration; and means disposed entirely circumferentially about and along the exterior of both ends of the endovascular support device for increasing the amount of force needed to expand both ends of the endovascular support device from the force needed to expand the medial region.

16. A stent-graft assembly comprising:

a first generally cylindrical stent having a length, first and second ends, an exterior and an interior, and a medial region, said first generally cylindrical stent defining a passageway therethrough;

a second generally cylindrical stent disposed radially outwardly and overlapping one end of the first stent;

a third generally cylindrical stent having a length and disposed radially outwardly and overlapping the second end of the first stent; and a lining having a first and second end and covering at least a portion of the exterior of the first stent, and having one end thereof disposed between the first and second stents.

17. The stent-graft assembly according to claim 16 wherein the first end of lining is disposed between the first and second stents and the second end of the lining is disposed between the first and third stents.

18. The stent-graft assembly according to claim 16 wherein the second generally cylindrical stent is connected to the first stent at the first end of the first stent, and the third generally cylindrical stent is connected to the first stent at the second end of the first stent.

19. The stent-graft assembly according to claim 16 wherein the length of second generally cylindrical stent and the length of the third generally cylindrical stent are each less than half of the length of the first stent.

20. The stent-graft assembly according to claim 16 wherein the lining is a polymer selected from the group consisting of polyurethane, ePTFE, dimethyl terephthalate, polyester, polyethylene terephthalate and silicone.

* * * * *